(12) United States Patent
Sommer et al.

(10) Patent No.: US 6,377,343 B1
(45) Date of Patent: Apr. 23, 2002

(54) VESSEL SYSTEM FOR MONITORING OF FLUID SAMPLES

(75) Inventors: Detlef Sommer, Ahrensburg; Eckhard Nehring, Kisdorf; Gerd Buettner, Henstedt-Ulzburg, all of (DE)

(73) Assignee: Bran + Luebbe GmbH, Norderstedt (DE)

( * ) Notice: Subject to any disclaimer, the term of this patent is extended or adjusted under 35 U.S.C. 154(b) by 0 days.

(21) Appl. No.: 09/463,930

(22) PCT Filed: Aug. 4, 1997

(86) PCT No.: PCT/EP97/04234

§ 371 Date: Mar. 31, 2000

§ 102(e) Date: Mar. 31, 2000

(87) PCT Pub. No.: WO99/08094

PCT Pub. Date: Feb. 18, 1999

(51) Int. Cl.[7] .................................................. G01N 1/10
(52) U.S. Cl. ....................................... 356/246; 356/326
(58) Field of Search .................................. 356/246, 300, 356/326, 331; 250/216, 239, 432 R, 435, 576; 422/68.1, 82.05, 82.08, 82.09; 433/165, 52; 251/149, 149.1, 149.6, 149.9; 137/614, 614.02, 614.05, 614.06

(56) References Cited

U.S. PATENT DOCUMENTS 3,973,752 A * 8/1976 Boelkins .................. 251/149.6
4,192,614 A * 3/1980 DeMey, II et al. ......... 356/410
5,407,638 A * 4/1995 Wang ....................... 422/82.09
5,442,437 A * 8/1995 Davidson ................... 356/246

FOREIGN PATENT DOCUMENTS

| DE | 28 46 740 A1 | * | 10/1980 |
| EP | 0 369 310 A | * | 5/1990 |
| EP | 0 476 088 B1 | | 5/1995 |
| EP | 0 710 836 A | * | 8/1996 |

* cited by examiner

*Primary Examiner*—Frank G. Font
*Assistant Examiner*—Michael P. Stafira
(74) *Attorney, Agent, or Firm*—Michael J. Striker

(57) ABSTRACT

The invention relates to a vessel system for the continuous monitoring of fluids, in particular in industrial processes, preferably by means of NIR spectroscopy, with a vessel that is disposed in a subassembly support and has an inlet opening and outlet opening as well as a beam path directed at the sample chamber. In order to facilitate maintenance, the provision is made that the subassembly support is disposed in a housing with an inlet armature and an outlet armature that pass through the housing, wherein rapidly detachable lines are provided between the inlet and outlet armature of the housing and the inlet and outlet opening of the sample chamber.

11 Claims, 3 Drawing Sheets

VESSEL SYSTEM FOR MONITORING OF FLUID SAMPLES

Figure 1:
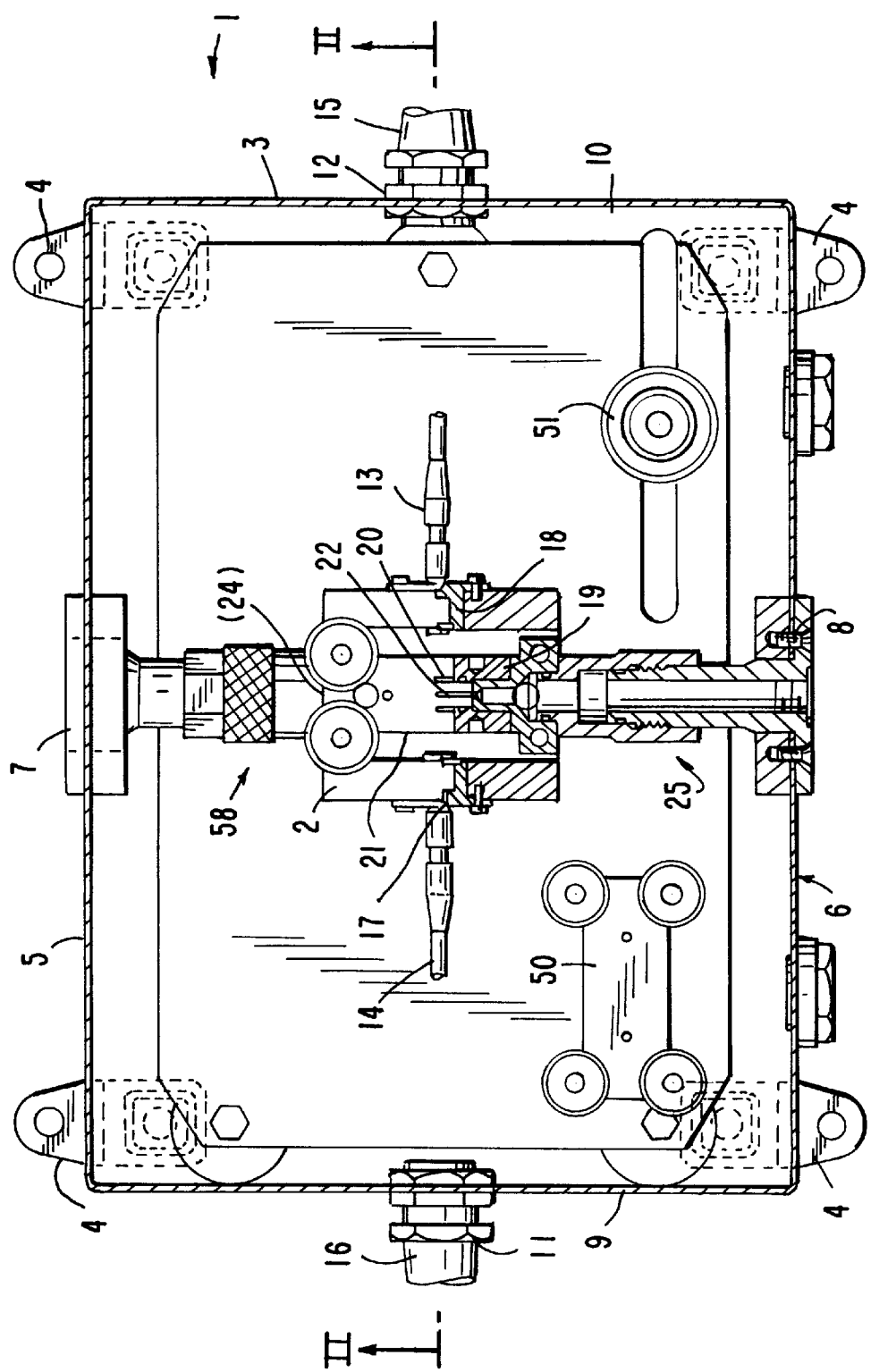

The invention relates to a vessel system for the continuous monitoring of fluids, in particular industrial processes, preferably by means of NIR spectroscopy, having a vessel that is disposed in a subassembly support and has a sample chamber with an inlet opening and an outlet opening as well as a beam path directed toward a window of the sample chamber.

A vessel system of this kind has been disclosed, for example, by the European patent EP-B1-0 476 088 of the applicant.

Vessel systems of this kind are used for the online monitoring of fluids samples, in order to monitor the operation of systems. To this end, the sample is conveyed through a sample chamber that has a definite through flow gap, which is constituted by two disks that are spaced apart from each other. A beam of a light source is directed at the sample from one side and the beam is connected to a receiver on the other side, after it has passed through the sample. The composition of the sample can be deduced from the extinction of particular wavelengths.

In other systems, instead of the second disk, a reflective surface can also be used so that the composition of the sample can be deduced from the spectral composition of the reflected NIR (near infrared red) spectrum.

In order for reproducible measurement results to be produced, it is very important that the optical structure of the system does not get moved. Furthermore, the distance between the disks, i.e. the through flow gap or the layer thickness of the sample, has a significant influence on the measurement result. This layer thickness must also have the capacity for being set in a reproducible fashion. Finally, it is necessary to prevent deposits from forming on the measurement window which can also lead to distortions of the measurement result.

It is therefore important to carefully maintain systems of this kind and to clean them as needed.

Furthermore, the system must also be able to withstand the temperatures and pressures that prevail in harsh industrial operation in the manufacture of products, which need to be analyzed in an online fashion, i.e. continuously, by the system.

It also happens that different products are produced in the system to which the measuring device belongs. In such instances, it is necessary that the layer thickness can also be adapted to the medium to be analyzed.

Furthermore, is also necessary to measure reference samples with the system in order to calibrate the signal processing chain.

In the case of an instrument for laboratory operation, as is described in a product pamphlet of the applicant under the product name "InfaPrime Lab", a subassembly support is provided in a housing in which a standard glass vessel can be removed from the support and replaced by another standard vessel with a different layer thickness. As a result, it is possible to replace the vessel with a vessel that is similar, but is provided for other mediums.

In the support, therefore, the opening for the vessel is provided so that it is larger than would be necessary for most vessels. The gap in relation to the support, which gap is therefore produced with smaller dimensions, is bridged over by an adapter piece or a spacer.

With this embodiment, it has turned out to be disadvantageous that only standard laboratory vessels can be used. Furthermore, before the vessel replacement, the lines must be detached in an expensive manner. The housing is detached and rests on the table. Both the vessels and the supply lines are not suitable for industrial use. The medium to be analyzed must be supplied at low pressure by means of corresponding pumps, usually hose pumps.

By contrast, the system according to European patent EP-B1-0 476 088 is suitable for industrial conditions. A system of this kind is rigidly connected in the system by means of pipes. However, it must be disassembled in a very expensive manner for maintenance and must be carefully adjusted and installed in the system once again after maintenance. Particular care must be exercised in the fastening of light wave conductors since changes in the beam path, as explained above, can lead to distortions of the measurement result.

The object of the invention is to supply a system of the generic type mentioned at the beginning, which makes it possible to carry out monitoring under industrial conditions with a simplified maintenance.

This object is attained with a vessel system of this generic type by virtue of the fact that the subassembly support is disposed in a housing with a connecting armature that passes through the housing, wherein lines are provided between the connecting armature of the housing and the inlet and outlet openings of the sample chamber. The housing can consequently be rigidly installed in the system. All of the necessary pipelines of the system are rigidly connected to the housing.

The housing can advantageously be embodied in an explosion-proof manner so that the vessel system can also be used in an environment in which there is the danger of explosions. In order to perform maintenance or to replace the vessel, the connections inside the housing need only be detached and reassembled after the replacement of the vessel.

The replacement or maintenance of the vessel is embodied in a particularly simple fashion if the lines are embodied so that they can be detached quickly.

Additional assembly costs can be prevented if the vessel is embodied so that it can be removed as a subassembly from the subassembly support. By means of this, namely the connections of light wave conductors to the subassembly support can remain in place. A readjustment of the optics after the replacement of the vessel is advantageously eliminated since the subassembly support remains connected to the light wave conductors during the vessel replacement.

In terms of construction, it is sufficient for the rapid detachment of the line from the vessel if the line is comprised of an axially adjustable pipe end and a stationary pipe end that is preferably attached to the housing, which are embodied so that they can telescope in relation to each other.

Advantageously, the axial adjustment can occur by virtue of the fact that the line is embodied as a resilient tubular spiral and/or as an axially resilient bellows and/or as a resilient tubular meander and/or as a hose loop.

A knuckle joint is provided for rapid axial adjustment.

In an alternative embodiment, a spindle nut actuator is provided for the axial adjustment.

In particular applications in which particularly frequent maintenance is required due to the mediums to be analyzed and in which compressed air is already available in the system, it can be advantageous if a piston/cylinder drive mechanism is provided for the axial adjustment.

The measure that the subassembly support has an optical subassembly for the connection of a light wave conductor for the purpose of coupling and decoupling for radiation, permits a pre-assembly of the coupling and decoupling optics, for example for changed mediums. The optical conditions can be easily adapted to changed mediums or measuring methods, for example to a reflection measurement, through replacement of the optical subassembly.

Advantageously, the housing is embodied so that it is large enough for an assembly tool to be disposed in the housing. As a result, all of the tools required for replacement and for maintenance are always on hand. In addition to planned maintenance intervals, this also permits a maintenance or a replacement of the vessel to be carried out without incurring high costs.

The subassembly support can also be advantageously embodied so that the subassembly support has optical subassemblies for connecting a reference beam path. In order to improve measurement precision, before reaching its path through the sample, a reference beam is given an optical path that is largely equivalent to that of the measurement beam. As a result, influences of the optical components on the measurement result can be prevented through comparison of the signals.

If the sample chamber is embodied as guided, then optical conditions prevail which are always reproducible so that even after maintenance and assembly, a re-calibration can be advantageously eliminated.

The replacement is easier to carry out if a valve is integrated into the connecting armature.

An escape of the medium to be analyzed from the fixed piping into the housing is prevented if the valve is designed to close automatically when the line is detached.

When the medium to be analyzed is changed, the optical conditions for the measurement can be optimized by virtue of the fact that the through flow gap of the sample chamber is embodied so that can be adjusted. A spacer is disposed in the measurement chamber and reproducibly adjusts the gap for the through flow of the medium.

In particular instances it is advantageous that the sample chamber is embodied so that it is thermally insulated and/or temperature-stabilized, preferably by means of a temperature regulation. The this can be achieved, for example, by virtue of the fact that the contact surfaces in relation to the subassembly support are reduced to a minimum or else the sample chamber or the entire housing is kept at a constant temperature by means of a regulation.

The invention will be described in conjunction with a preferred embodiment form with reference to a drawing, wherein other advantageous details can be inferred from the figures of the drawing.

Parts which function in the same manner are provided with the same reference numerals.

Figure 2:
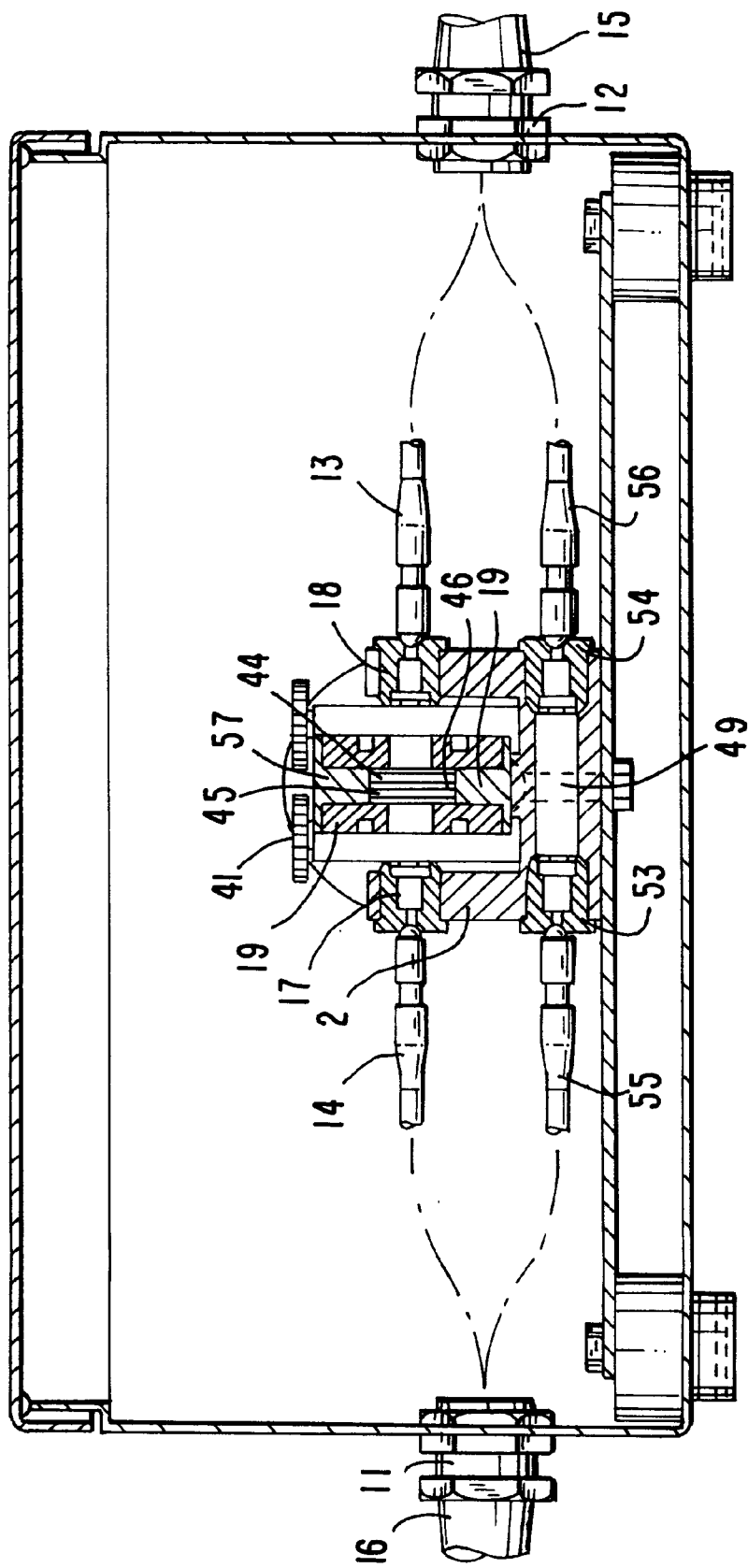
Figure 3:
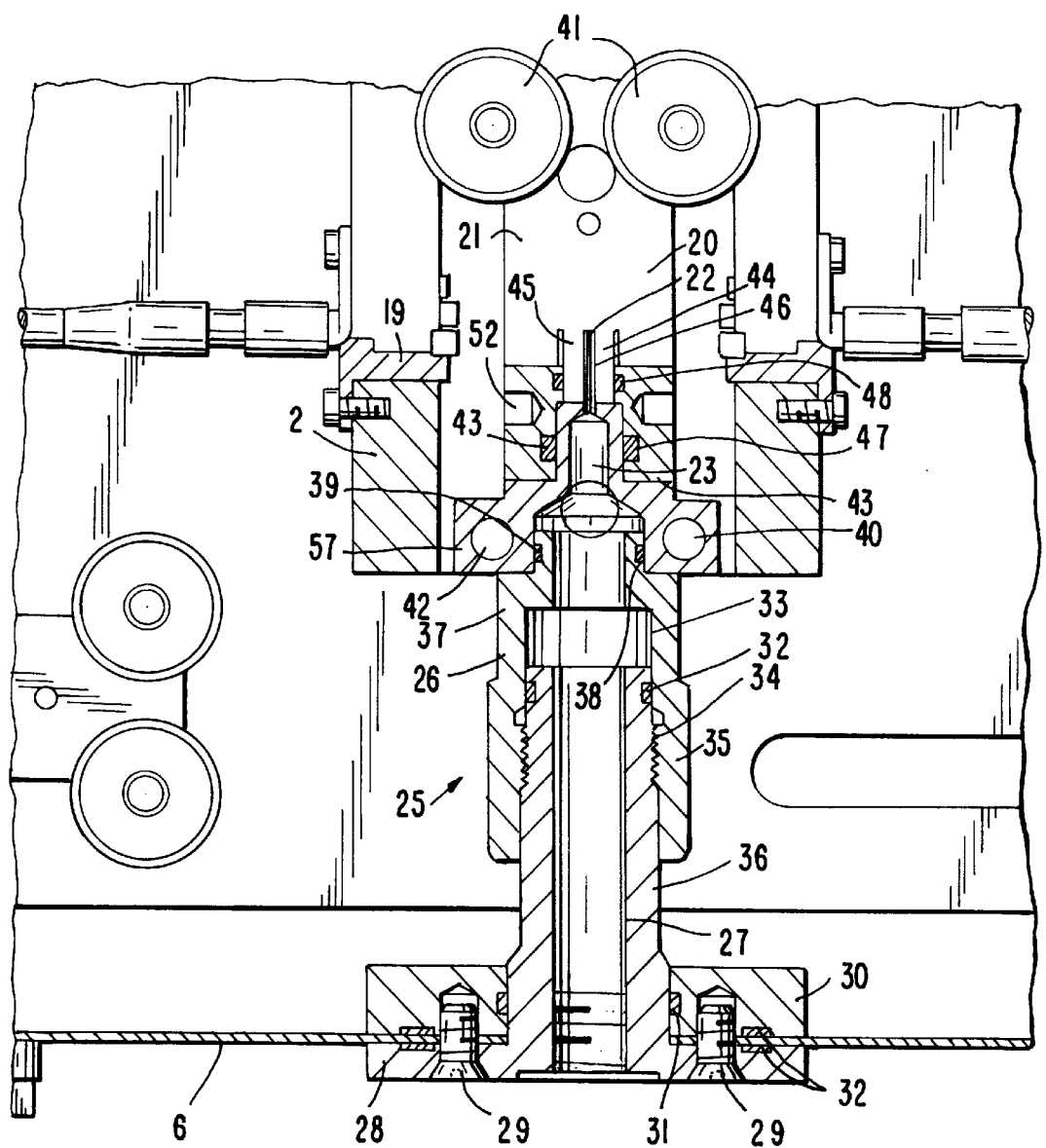

FIG. 1 is a top view of the vessel system according to the invention without a cover, FIG. 2 shows a section through the vessel system according to the invention, in accordance with the cutting line II—II in FIG. 1, and FIG. 3 shows a detail from FIG. 1.

In FIG. 1, the vessel system according to the invention is labeled with the reference numeral 1. It is comprised of the subassembly support 2, which is rigidly mounted inside a housing 3. The housing 3 has external fastening tabs 4 with which it is rigidly mounted in a system. The connecting armatures 7 and 8 pass through the upper wall 5 and the lower wall 6. The pipelines which convey the medium to be analyzed and are not shown here, are routed to these armatures 7, 8 and connected to the armatures 7, 8.

Furthermore, screwed cable glands 11 and 12 are shown in the left wall 9 and right wall 10, by means of which the light wave conductors 13 and 14 are guided into the housing.

An antikink device 15, 16 on the screwed cable glands 11, 12 protects the light wave conductors, which are screw-connected to the optical subassemblies 17, 18 by means of known screw connections. The optical subassemblies 18, 17 are in turn screw connected to the subassembly support 2. The light wave conductor 13 conveys the light to a vessel 19.

The vessel in turn has an irradiation window 20 and an outlet window 21, between which a sample chamber 22 is formed. The beam emerging from the light wave conductor passes through the sample chamber 22. The emerging light is captured by the optical subassembly 17 and coupled into the light wave conductor 14, which conveys the light to a receiver whose signal is processed by a known measurement chain to produce the measured spectrum.

For the medium to be analyzed, the sample chamber 22 has an inlet opening 23 and a symmetrically embodied outlet opening 24, which is visible underneath the center line in the depiction of a horizontal section shown. The connection between the armatures 7, 8 and the openings 23, 24 of the sample chamber 22 is produced by means of the lines 25, 58.

The line 25 is shown as a detail in an enlarged depiction in FIG. 3.

It is comprised of an axially movable pipe end 26, which can be adjusted in telescope fashion in relation to a stationary pipe end 27.

The stationary pipe end 27 has a flange 28, which clamps the pipe end 27 in the opening of the lower wall by means of screws 29 and a clamping ring 30. Sealing is performed by an O-ring 31, which seals the pipe end 27 in relation to the clamping ring 30 and by the two annular seals 32, which seal the flange 28 and the clamping ring 30 in relation to the lower wall 6. The movable pipe end 26 has a cylindrical bore 33 with which it can move axially on a cylindrical section 34 of the stationary pipe end 27 that is adapted to it. In this connection, an O-ring 32 seals the gap between the cylindrical section 34 of the stationary pipe end and the cylindrical bore 30. The lower end of the pipe end 26 has a section with a bore 35, which is screwed like a nut onto a corresponding externally threaded section 36 of the pipe end 27. A cylindrical outer surface 37 is formed onto the upper end of the pipe end 26 and is introduced into an adapted cylindrical inner surface 38 of the vessel 19. The sealing gap between these surfaces is sealed by the O-ring 39. The cylindrical inner surface 38 connects the connecting armature as a line to the inlet opening 23 of the sample chamber 22.

If the pipe end 26 is rotated then it also moves axially in accordance with the pitch of the threaded section 31. As a result, the outer surface 37 travels out of the cylindrical inner surface 38 and thereby detaches the vessel 19 from the housing 3.

In the vicinity of its outer corners, the vessel 19 has guide services 40 embodied as bores which are engaged by correspondingly formed guide pins 42 of the subassembly support 2. At their upper ends, the guide pins 42 have a thread which the nuts 41 are screwed onto. The vessel is consequently clamped firmly to the subassembly support 2 by means of the guide pins 42 and nuts 41. After removal of the screws 41 and unscrewing of the pipe end 26, the vessel 19 can be removed and replaced by a new vessel.

The vessel 19 is comprised of a block 57, which has the opening 23 for the inlet of the medium and the opening 24 for the outlet of the medium let into it. Screw connected, annular disk-shaped window frames 43, which are provided on both sides of the through flow openings 23, 24, secure disks 45, which form an inlet window 20 and an outlet window 21, wherein a spacer 46 is disposed between these disks. The seals 47 and seal 48 seal the disks of the sample chamber 22 and the block 57 in relation to the window frame 43.

The contacting surfaces of the block 57 in relation to the subassembly support 2 are reduced to a minimum so that the sample chamber is thermally insulated to the greatest degree possible from the rest of the parts.

The internally threaded section 35 and the corresponding externally threaded section 34, which serve as a guide and as a driving mechanism for the axial retraction, can also be replaced, for example, by guide surfaces and a suitable linear mechanism. For example, a specialist can provide a piston/cylinder unit as a linear mechanism or can provide a knuckle joint, which moves the axially movable pipe end 26 after the fashion of a quick-acting clamp.

A replacement vessel 50 is fastened inside the housing 3 and can be used to replace the vessel 19 that requires maintenance. A tool 51 is also provided in the housing and this tool, with its appropriately disposed pins (not visible), is suited for engaging in bores 52 of the window frame 43. The tool 51 is used to unscrew the window frame from the block 42 in order to then clean the removable disks 44, 45.

Optical subassemblies 53, 54 are also provided in a bore 49 and are used to connect additional light wave conductors 55, 56, which serve as a reference beam path.

In this manner, a vessel system has been produced which is significantly easier to maintain and can be rigidly mounted in industrial systems so that it is even suitable for operating environments in which there is the danger of explosions.

Reference numeral list 1 vessel system
2 subassembly support
3 housing
4 fastening tabs
5 upper wall
6 lower wall
7 connecting armature for outlet
8 connecting armature for inlet
9 left wall
10 right wall
11 screwed cable gland
12 screwed cable gland
13 light wave conductor
14 light wave conductor
15 antikink device
16 antikink device
17 optical subassembly
18 optical subassembly
19 vessel
20 irradiation window
21 outlet window
22 sample chamber
23 inlet opening
24 outlet opening
25 line
26 movable pipe end
27 stationary pipe end
28 flange
29 screw
30 clamping ring
31 O-ring
32 seal
33 cylindrical bore
34 cylindrical section
35 bore
36 externally threaded section
37 outer surface
38 cylindrical inner surface
39 O-ring
40 guide surface
41 nut
42 guide pin
43 window frame
44 disk
45 disk
46 spacer
47 seal
48 seal
49 bore
50 replacement vessel
51 tool
52 bore
53 optical subassembly
54 optical subassembly
55 light wave conductor
56 light wave conductor
57 block

What is claimed is:

1. A vessel system for the continuous monitoring of fluids in industrial processes by means of NIR spectroscopy, with a vessel that is disposed in a subassembly support and has a sample chamber with an inlet opening and an outlet opening as well as a beam path directed at a window of the sample chamber, characterized in that the subassembly support (2) is disposed in a housing (3) with a connecting armature (7, 8) that passes through the housing (3), wherein a first line is provided between a first connecting armature of the housing and the inlet opening of the sample chamber and a second line is provided between a second connecting armature of the housing and the outlet opening of the sample chamber and wherein the vessel can be removed as a subassembly from the subassembly support (2) and wherein the subassembly support (2) has optical subassemblies (17, 18, 53, 54) for the connection of light wave conductors (13, 14, 55, 56) for the purpose of coupling and decoupling radiation and wherein the subassembly support (2) is rigidly mounted in the housing (3) and wherein the vessel (19) is guided.

2. The vessel system according to claim 1, characterized in that the lines (25, 26) are embodied with an axially movable, rapidly detachable connection to the openings (23, 24) of the sample chamber (22).

3. The vessel system according to claim 1, characterized in that the lines (25, 58) are comprised of an axially movable pipe end (26) and a stationary pipe end (27) fastened to the housing (3), which can telescope in relation to each other.

4. The vessel system according to claim 1, characterized in that the lines are each a resilient tubular spiral or an axially resilient bellows or a resilient tubular meander or a hose loop.

5. The vessel system according to claim 1, characterized in that a knuckle joint or a spindle nut actuator or a piston/cylinder drive is provided for axial adjustment.

6. The vessel system according to claim 1, characterized in that a mounting tool (51) is disposed in the housing (3).

7. The vessel system according to claim 1, characterized in that the subassembly support (2) has optical subassemblies (53, 54) for the connection of a reference beam path.

8. The vessel system according to claim 1, characterized in that a valve is integrated into the connecting armatures or lines (25, 58).

9. The vessel system according to claim 1, characterized in that the valve automatically closes when the lines (25, 58) is detached.

10. The vessel system according to claim 1, characterized in that the sample chamber (22) has a through flow gap whose spacing is embodied so that it can be adjusted.

11. The vessel system according to claim 1, characterized in that the sample chamber (22) is embodied as thermally insulated and/or temperature-stabilized, preferably by means of a temperature regulation.

* * * * *